Sept. 17, 1974 F. W. ANDERSON Plant Pat. 3,617
PLUM TREE
Filed Aug. 8, 1973
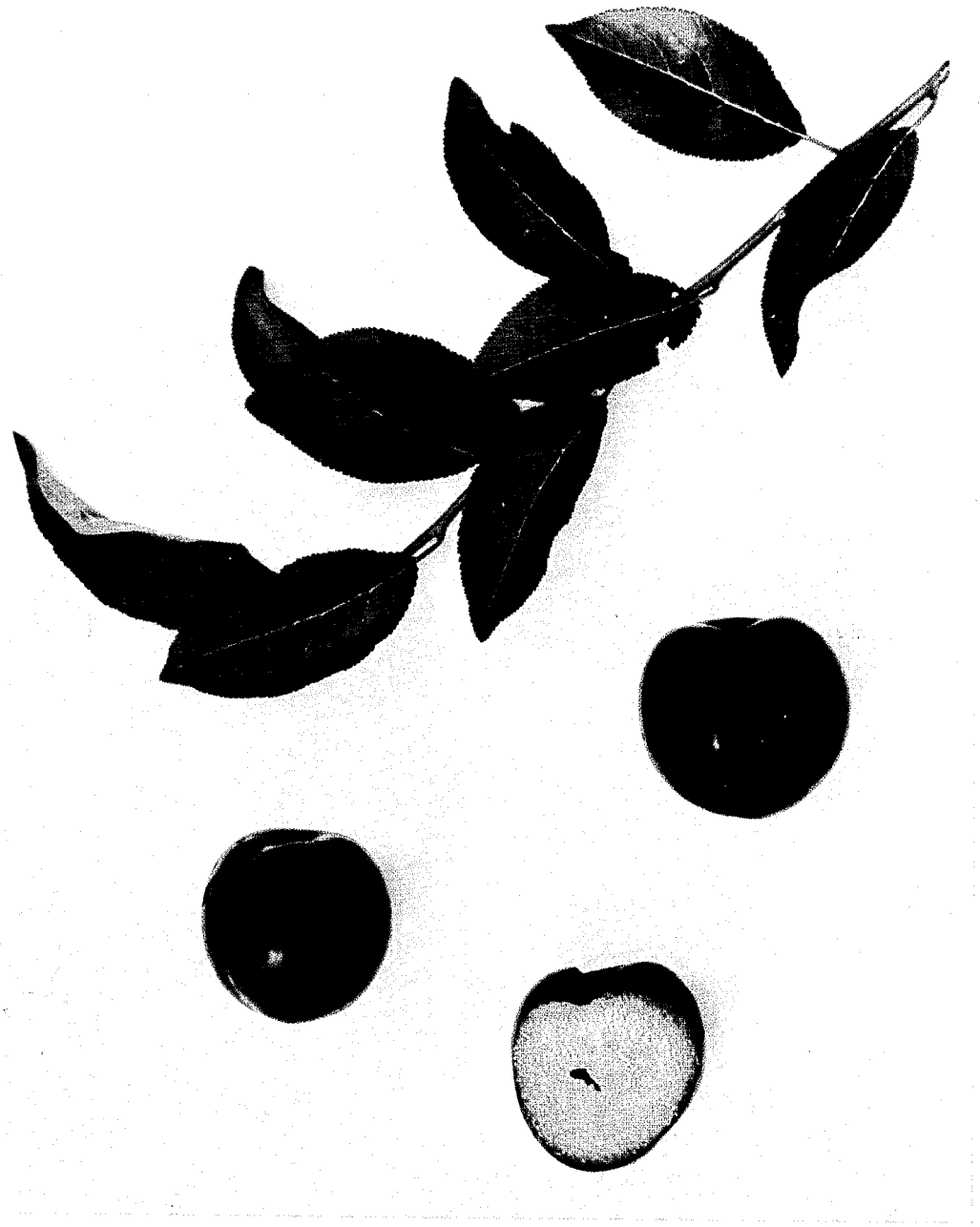

United States Patent Office

Plant Pat. 3,617
Patented Sept. 17, 1974

3,617
PLUM TREE

Frederic W. Anderson, Merced, Calif., assignor to Reedley Nursery, Inc., Reedley, Calif.

Filed Aug. 8, 1973, Ser. No. 386,735
Int. Cl. A01h 5/03
U.S. Cl. Plt.—38 1 Claim

ABSTRACT OF THE DISCLOSURE

A plum tree which is large, vigorous, upright to spreading, foliated with large to medium size obovate leaves, and a productive bearer of uniform, large to medium size, globose to slightly oblate, semi-freestone fruit having yellow to red flesh and very deep purple-blue skin.

*Background of the variety*: Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program.

*Origin of the variety*: The present variety of plum tree was originated by me, in my experimental nursery and orchard located as aforesaid, as an open-pollinated seedling of the Red Beaut (U. S. Plant Pat. No. 2,539).

*Asexual reproduction of the variety*: Upon recognition by me of the novel and distinctive characteristics of the present variety of plum tree, I asexually reproduced it by top-working on mature orchard trees in said experimental orchard, and—in maturity—such reproductions ran true to the parent tree in all respects.

*Summary of the variety*: The present variety of plum tree is large, vigorous, upright to spreading, foliated with large to medium size obovate leaves, and a productive bearer of uniform, large to medium size, globose to slightly oblate, semi-freestone fruit having yellow to red flesh and very deep purple-blue skin; the variety—which is generally similar to the Red Beaut—being essentially characterized, as to novelty, by fruit which ripens about ten days before the Santa Rosa (unpatented) and about ten days after the Red Beaut. This permits the harvest of the present variety to start immediately upon the last picking of the Red Beaut and so that the in-market season for such type of plum is desirably extended.

The present variety is further characterized, as to novelty, by fruit which is larger, darker in skin color, and more oblate than the fruit of the Red Beaut.

*Brief description of the drawing*: The drawing is an illustration, by photographic reproduction in color, of a twig with leaves, and separate fruit one of which is partially cut away to expose the flesh.

*Description of the variety*: The botanical details of this new and distinct variety of plum tree—with color definitions (except those in common color terms) referenced to Maerz and Paul Dictionary of Color—are as follows:

Tree:
- *Size.*—Large.
- *Vigor.*—Vigorous.
- *Form.*—Upright to spreading.
- *Productivity.*—Productive.

Trunk:
- *Size.*—Medium.
- *Texture.*—Medium.

Branches:
- *Size.*—Medium.
- *Texture.*—Medium.
- *Lenticels.*—Number: Medium. Size: Medium Leaves:
- *Size.*—Large to medium. Average length—3½". Average width—1¾".
- *Form.*—Obovate. Acutely pointed.
- *Thickness.*—Medium.
- *Texture.*—Smooth.
- *Color.*—Top side—Medium green (22–I–9). Under side—Lighter green (22–K–7).
- *Margin.*—Crenate.
- *Petiole.*—Medium length. Medium thickness.
- *Glands.*—Average number—2. Alternate. Globose. Positioned on petiole and base of blade.

Flower buds:
- *Length.*—Short.
- *Form.*—Obtuse.

Flowers:
- *Blooming Period.*—4 to 5 days after Red Beaut. Medium to late, as compared with other varieties.
- *Color.*—White.

Fruit:
- *Maturity When Described.*—Eating ripe—June 15th, 1973.
- *Date of First Picking.*—June 10th, 1973.
- *Date of Last Picking.*—June 17th, 1973.
- *Size.*—Uniform. Large to medium. Average diameter axially—2¼". Average transversely in suture plane—2".
- *Form.*—Globose to slightly oblate.
- *Suture.*—Distinct. Shallow. Extends from base to apex.
- *Ventral Surface.*—Rounded slightly.
- *Cavity.*—Rounded.
- *Apex.*—Very short to non-existent.

Skin:
- *Thickness.*—Medium.
- *Texture.*—Tough.
- *Tendency to Crack.*—None noted.
- *Down.*—Wanting.
- *Color.*—Deep purple-blue (48–H–12).

Flesh:
- *Texture.*—Medium. Crisp. Meaty. Melting.
- *Fibers.*—Few. Tender.
- *Ripens.*—Evenly.
- *Flavor.*—Delicate.
- *Eating Quality.*—Good.
- *Color.*—Yellow (11–K–4) to red.

Stone:
- *Type.*—Semi-free.
- *Size.*—Medium to small. Average length—¾". Average breadth—⅝". Average thickness—¼".
- *Color.*—Beige (13–H–7).

Use: Market—Long distance shipping.

Keeping quality: Very good.

Resistance to insects and diseases: No unusual susceptibilities noted.

Shipping quality: Excellent.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is large, vigorous, upright to spreading, foliated with large to medium size obovate leaves, and a productive bearer of uniform, large to medium size, globose to slightly oblate, semi-freestone fruit having yellow to red flesh and very deep purple-blue skin; the variety being particularly characterized in comparison to the Santa Rosa by fruit which ripens about ten days before the Santa Rosa, and in comparison to the Red Beaut by fruit which ripens about ten days later, is larger, darker in skin color, and more oblate.

No references cited.

ROBERT E. BAGWILL, Primary Examiner